United States Patent [19]

Tenten et al.

[11] Patent Number: 5,446,004
[45] Date of Patent: Aug. 29, 1995

[54] MULTIMETAL OXIDE COMPOSITIONS

[75] Inventors: Andreas Tenten, Neustadt; Peter Weidlich, Mannheim, both of Germany

[73] Assignee: BASF Aktiengesellschaft, Ludwigshafen, Germany

[21] Appl. No.: 187,494

[22] Filed: Jan. 28, 1994

[30] Foreign Application Priority Data

Feb. 3, 1993 [DE] Germany .................. 43 02 991.4

[51] Int. Cl.$^6$ .................. B01J 23/22; B01J 23/30
[52] U.S. Cl. .................. 502/312; 502/244; 502/247; 502/254; 502/259; 502/306; 502/308; 502/309; 502/311; 502/315; 502/317; 502/318; 502/328; 502/330; 502/331; 502/337; 502/340; 502/344; 502/345; 502/349; 502/350
[58] Field of Search ............... 502/312, 317, 318, 315, 502/330, 345, 209, 244, 247, 254, 259, 306, 308, 309, 311, 328, 331, 337, 340, 344, 349, 350

[56] References Cited

U.S. PATENT DOCUMENTS

| | | | |
|---|---|---|---|
| 4,075,127 | 2/1978 | Kadowaki et al. | 502/312 |
| 4,289,654 | 9/1981 | Bertolini et al. | |
| 4,358,608 | 11/1982 | Shaw et al. | |
| 4,380,672 | 4/1983 | Velenyi et al. | |
| 5,017,542 | 5/1991 | Martan et al. | 502/209 |
| 5,102,846 | 4/1992 | Kuroda et al. | 502/209 |
| 5,102,847 | 4/1992 | Yamamoto et al. | 502/205 |
| 5,173,468 | 12/1992 | Boehning et al. | 502/311 |

FOREIGN PATENT DOCUMENTS

| | | |
|---|---|---|
| 0017000 | 10/1980 | European Pat. Off. |
| 0052839 | 6/1982 | European Pat. Off. |
| 0235760 | 9/1987 | European Pat. Off. |

Primary Examiner—Anthony McFarlane
Attorney, Agent, or Firm—Oblon, Spivak, McClelland, Maier & Neustadt

[57] ABSTRACT

Multimetal oxide compositions which comprise, as basic constituents, the elements Mo, V, W, Cu and Ni in oxidic form in certain molar ratios, and the preparation of these multimetal oxide compositions, and their use as catalysts for the gas-phase catalytical oxidation of acrolein to acrylic acid.

8 Claims, No Drawings

MULTIMETAL OXIDE COMPOSITIONS

The present invention relates to multimetal oxide compositions which comprise, as basic constituents, the elements Mo, V, W, Cu and Ni in oxidic form, with the proviso that the following molar ratios exist between the various elemental constituents:

Mo:V = 12:1 to 2:1,
Mo:W = 60:1 to 3:1
Mo:Cu = 24:1 to 2:1 and
Cu:Ni = 5:1 to 1:3.

The present invention also relates to a process for the preparation of these compositions, and to their use.

EP-A 427 508, DE-A 29 09 671, DE-C 31 51 805 and DE-B 26 26 887 disclose multimetal oxide compositions which comprise, in addition to other elemental oxides, the elements Mo, V, W and Cu in oxidic form as basic constituents. Examples which are disclosed include multimetal oxide compositions in which the molar constituent ratios Mo:V, Mo:W and Mo:Cu are in the range defined according to the invention. These multimetal oxide compositions are recommended, inter alia, as catalysts for the catalytic gas-phase oxidation of acrolein to acrylic acid.

In this application, however, these multimetal oxide compositions are not fully satisfactory in respect to activity and selectivity of acrylic acid formation. Furthermore, these multimetal oxide compositions only achieve their final selectivity (for a given conversion) for the formation of acrylic acid after an extended operating time.

EP-A 235 760 discloses multimetal oxide compositions which are suitable as catalysts for the gas-phase catalytic oxidation of acrolein to acrylic acid and which contain Ni in oxidic form as a further basic constituent in addition to the elements Mo, V, W and Cu. However, these multimetal oxide compositions have the disadvantage that the molar ratio between the elemental constituent Cu and the elemental constituent Ni in them is less than 1:3, which means that these multimetal oxide compositions are also not entirely satisfactory with respect to use for the catalytic gas-phase oxidation of acrolein to acrylic acid.

It is an object of the present invention to provide multimetal oxide compositions which are more satisfactory for use as catalysts for the gas-phase catalytic oxidation of acrolein to acrylic acid.

We have found that this object is achieved by the compositions defined at the outset.

Preference is given to multimetal oxide compositions according to the invention in which the molar ratio between the elemental constituent Cu and the elemental constituent Ni is from 3:1 to 1:2, particularly preferably 2:1.

Particularly advantageous compositions according to the invention are those which conform to the empirical formula I

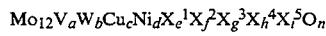 (I)

where
$X^1$ is one or more alkali metals,
$X^2$ is one or more alkaline earth metals,
$X^3$ is chromium, manganese, cerium and/or niobium,
$X^4$ is antimony and/or bismuth,
$X^5$ is silicon, aluminum, titanium and/or zirconium,
a is from 1 to 6,
b is from 0.2 to 4,
c is from 0.5 to 6,
d is from 0.2 to 6,
c:d is from 5:1 to 1:3,
e is from 0 to 2,
f is from 0 to 3,
g is from 0 to 5,
h is from 0 to 40,
i is from 0 to 40 and
n is a number which is determined by the valency and frequency of the elements in I other than oxygen.

Of these, preference is in turn given to those in which the stoichiometric coefficients e, f, g and h are 0.

The compositions according to the invention are generally prepared in a manner known per se by producing a very intimate dry mix of suitable starting compounds which contain the elemental catalyst constituents and calcining this dry mix at from 200° to 500° C., preferably at from 300° to 400° C. The only essential feature is that the starting compounds employed are either already oxides or are compounds which can be converted into oxides by heating, in the presence or absence of oxygen. In addition to metal oxides, suitable starting compounds are therefore, in particular, halides, nitrates, formates, acetates, carbonates and hydroxides. Suitable starting compounds of Mo, W and V are also their molybdates, tungstates and vanadates, or the acids derived therefrom.

The intimate mixing of the starting compounds can be carried out in dry or wet form. If it is carried out in dry form, the starting compounds are expediently employed as finely divided powders and after the mixing are pressed (for example tabletted), for example to give catalyst bodies of the desired geometry, which are then subjected to calcination.

However, the intimate mixing is preferably carried out in wet form. In this case, the starting compounds are usually mixed with one another in the form of an aqueous solution or suspension. The aqueous composition is then dried and calcined.

The drying process is preferably carried out immediately after preparation of the aqueous mixture and is accomplished by spray drying (starting temperatures are generally from 100° to 150° C.). The powder thus produced can be shaped directly by pressing. Frequently, however, it proves to be too finely divided for direct further processing; it is therefore expediently first kneaded with addition of water.

The kneading composition produced is subsequently either shaped to the desired catalyst geometry, dried and then calcined (gives unsupported catalysts) or calcined without shaping and then ground to give a finely divided powder (usually <80 µm), which, normally with addition of a small amount of water and, if desired, further conventional binders, is applied as a moist composition to an inert support. Completion of the coating operation is followed by further drying, giving the ready-to-use shell catalyst. In principle, however, the calcined powder can also be employed as a powder catalyst.

In the case of aqueous wet mixing of the starting compounds, the starting compounds of the constituents Cu and Ni are preferably water-soluble copper and nickel salts, such as nitrates or acetates, the acetates being particularly advantageous. It is of course also possible for the acetates to be formed in situ during the mixing (for example by using carbonates as starting compounds and adding acetic acid).

In the case of unsupported catalysts, the stoichiometric coefficient i in the empirical formula I is advantageously from 15 to 40. Otherwise, i preferably has the value 0, since the oxides of constituent $X^5$ are those which essentially only result in dilution of the remainder of the composition.

If the starting compounds are mixed in the form of an aqueous solution, it is also possible for inert porous supports to be impregnated therewith, dried and subsequently calcined to give supported catalysts. Unsupported catalysts preferably have a geometry corresponding to hollow cylinders, as described in DE-A 31 13 179.

However, when the multimetal oxide compositions according to the invention are used as catalysts for the gas-phase catalytic oxidation of acrolein to acrylic acid, they are preferably used in the form of shell catalysts. The conventional support materials, such as porous or non-porous aluminum oxides, silicon dioxide, thorium dioxide, zirconium dioxide, silicon carbide or silicates, such as magnesium silicate or aluminum silicate, can be used. The supports may have a regular or irregular shape; regular supports with a distinct surface roughness, for example beads or hollow cylinders, are preferred. Of these, beads are in turn particularly advantageous. Very particularly advantageous is the use of essentially non-porous, surface-rough, spherical supports made from steatite, whose diameter is from 1 to 6 mm, preferably from 4 to 5 mm. The coating thickness of the active composition is expediently selected in the range from 50 to 500 μm, preferably in the range from 150 to 250 μm. It should be pointed out at this point that, in the preparation of shell catalysts, the coating of the supports can also be carried out before the calcination, ie., for example, using the moistened wettable powder.

The calcination of the dry composition containing the starting compounds in an intimate mixture is advantageously carried out in a rotary kiln charged with air.

The coating of the support elements for the preparation of shell catalysts is generally carried out in a suitable rotatable vessel, as disclosed, for example, in DE-A 29 09 671 or EP-A 293 859.

The starting compounds, the coating process and the calcination conditions are advantageously selected in a manner known per se in accordance with EP-A 293 859 in such a way that the resultant multimetal oxide active compositions have a specific surface area of from 0.50 to 150 m$^2$/g, a specific pore volume of from 0.10 to 0.90 cm$^3$/g and a pore diameter distribution such that in each case at least 10% of the total pore volume falls within the diameter ranges from 0.1 to <1 μm, from 1.0 to <10 μm and 10 μm to 100 μm. The pore diameter distributions mentioned as being preferred in EP-A 293 859 are preferably established.

The multimetal oxide compositions according to the invention are particularly suitable as catalysts having increased activity and selectivity for the gas-phase catalytic oxidation of acrolein to acrylic acid. The acrolein employed is preferably the product of an appropriate catalytic gas-phase oxidation of propene. The gas-phase catalytic oxidation of acrolein is usually carried out as a heterogeneous fixed-bed oxidation in tube-bundle reactors. The oxidant employed is conventionally oxygen, expediently diluted with inert gases. Examples of suitable inert gases are N$_2$ and/or steam. The reactant temperature and pressure are known to persons skilled in the art (cf. DE-A 41 32 263). It is noteworthy that the multimetal oxide catalysts according to the invention have a reduced activation time with respect to the selectivity for the formation of acrylic acid, ie. if a tube-bundle reactor charged with the compositions according to the invention is operated under conditions known per se to a person skilled in the art with an acrolein-containing gas stream for the purposes of oxidative formation of acrylic acid, the selectivity of the formation of acrylic acid increases to a maximum plateau level within a reduced operating time.

However, the multimetal oxide compositions according to the invention are also suitable for the gas-phase catalytic oxidation of other organic compounds, such a alkanes, alkanols, alkanals, alkenes and other alkenals to olefinically unsaturated aldehydes and/or carboxylic acids, and the corresponding nitriles (ammonoxidation, for example of propene to acrylonitrile and of 2-methylpropene or tert-butanol to methacrylonitrile). The number of carbon atoms in said organic compounds is normally in the range from 3 to 6, preferably 3 or 4.

EXAMPLES a) General procedure for the preparation of multimetal oxide compositions As a comparative example, a catalytically active composition C1 having the composition $Mo_{12}V_3W_{1.2}Cu_{2.4}O_x$ was prepared as follows:

190 g of copper(II) acetate monohydrate were dissolved in 2700 g of water to give a solution I. 860 g of ammonium heptamolybdate tetrahydrate, 143 g of ammonium metavanadate and 126 g of ammonium paratungstate heptahydrate were dissolved one after the other in 5500 g of water at 95° C. to give a solution II. Solution I was subsequently stirred in one portion into solution II, and the aqueous mixture was spray-dried at an outlet temperature of 110° C. The wettable powder was then compounded with 0.15 kg of water per kg of powder. The composition was heated to 400° C. over the course of 3 hours in an air-charged rotary kiln and subsequently calcined to 400° C. for 5 hours. The calcined, catalytically active material was ground to a particle diameter of from 0.1 to 50 μm.

Entirely analogously, multimetal oxide powders of the following compositions were prepared (Ni is employed as nickel (II) acetate tetrahydrate):

| | |
|---|---|
| $Mo_{12}V_3W_{1.2}Cu_{1.6}Ni_{0.8}O_x$ | (E1) |
| $Mo_{12}V_3W_{1.2}Cu_{0.8}Ni_{1.6}O_x$ | (E2) |
| $Mo_{12}V_3W_{1.2}Ni_{2.4}O_x$ | (C2) |
| $Mo_{12}V_3W_{1.2}Cu_{2.0}Ni_{0.4}O_x$ | (E3) |
| $Mo_{12}V_3W_{1.2}Cu_{2.4}Ni_{0.8}O_x'$ | (E4) |
| $Mo_{12}V_3W_{1.2}Cu_{1.6}O_x''$ | (C3) |
| $Mo_{12}V_3W_{1.2}Cu_{0.4}Ni_{2.0}O_x$ | (C4) | b) Preparation of shell catalysts

The active composition powders obtained in a) were coated in a rotary drum onto non-porous, surface-rough steatite beads having a diameter of from 4 to 5 mm in an amount of 50 g of powder per 200 g of steatite beads, with simultaneous addition of 18 g of water. The coating was subsequently dried by means of air at 110° C.

c) Gas-phase oxidation of acrolein

A reaction tube (V2A, 2 mm wall thickness) having a free diameter of 25 mm was in each case filled with 1 l of a mixture comprising the shell catalysts obtained in b) and an inert diluent material., and was heated by means of a salt bath. It was then charged with 2300 l(s.t.p.)/h of a gas mixture having the composition 5% by volume of acrolein, 7% by volume of oxygen, 10% by volume of steam and the remainder of nitrogen.

The salt-bath temperature was in all cases set so that an acrolein conversion of about 99mol% resulted after a single passage. The salt-bath temperatures necessary in this respect as a function of the shell catalyst employed in each case after an operating time of 3 weeks (measure of the activity; lower salt-bath temperatures indicate increased activities) and the resultant selectivities (based on acrylic acid formed) are shown in the table. The table also shows the activation times determined for the acrylic acid selectivity.

TABLE

| Catalyst | Acrolein conversion [mol %] | Salt-bath temperature [°C.] | selectivity [mol %] | Activation time [days] |
| --- | --- | --- | --- | --- |
| C1 | 99.1 | 275 | 95.0 | 10 |
| E1 | 99.0 | 264 | 96.2 | 2 |
| E2 | 98.9 | 265 | 95.8 | 3 |
| C2 | 98.2 | 283 | 94.3 | 3 |
| E3 | 99.1 | 267 | 95.7 | 3 |
| E4 | 98.9 | 265 | 95.6 | 4 |
| C3 | 99.0 | 267 | 95.3 | 8 |
| C4 | 98.5 | 279 | 94.5 | 3 |

We claim:

1. A multimetal oxide composition which comprises, as basic constituents, the elements Mo, V, W, Cu and Ni in oxidic form, with the proviso that the following molar ratios exist between the various elemental constituents:

Mo:V = 12:1 to 2:1,
Mo:W = 60:1 to 3:1,
Mo:Cu = 24:1 to 2:1, and
Cu:Ni = 5:1 to 1:3, which conforms to the empirical formula I

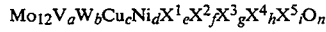

$$Mo_{12}V_aW_bCu_cNi_dX^1_eX^2_fX^3_gX^4_hX^5_iO_n$$

where $X^1$ is one or more alkali metals,
$X^2$ is one or more alkaline earth metals,
$X^3$ is chromium, manganese, cerium and/or niobium,
$X^4$ is antimony and/or bismuth,
$X^5$ is silicon, aluminum, titanium and/or zirconium,
a is from 1 to 6,
b is from 0.2 to 4,
c is from 0.5 to 6,
d is from 0.2 to 6,
c:d is from 5:1 to 1:3,
e is from 0 to 2,
f is from 0 to 3,
g is from 0 to 5,
h is from 0 to 40,
i is from 0 to 40 and
n is a number which is determined by the valency and occurrence of the elements in formula I other than oxygen.

2. The composition of claim 1, wherein the ratio Cu:Ni = 3:1 to 1:2.

3. The composition of claim 2, wherein the ratio Cu:Ni = 2:1.

4. The composition of claim 1, wherein said composition has a formula selected from the group consisting of $Mo_{12}V_3W_{1.2}Cu_{1.6}Ni_{1.8}O_x$, $Mo_{12}V_3W_{1.2}Cu_{0.8}Ni_{1.6}O_x$, $Mo_{12}V_3W_{1.2}Cu_{2.0}Ni_{0.4}O_x$, and $Mo_{12}V_3W_{1.2}Cu_{2.4}Ni_{0.8}O_x$, where x is a number which is determined by the valency and occurrence of the elements in formula I other than oxygen.

5. The composition of claim 1, wherein each of e, f, g, and h are zero.

6. A process for the preparation of a multimetal oxide composition which comprises, as basic constituents, the elements Mo, V, W, Cu and Ni in oxidic form, with the proviso that the following molar ratios exist between the various elemental constituents:

Mo:V = 12:1 to 2:1,
Mo:W = 60:1 to 3:1,
Mo:Cu = 24:1 to 2:1, and
Cu:Ni = 5:1 to 1:3, which comprises producing an intimate dry mix of starting compounds which contain the elemental multimetal oxide constituents, and calcining said dry mix at from 100° to 500° C.

7. The process of claim 6, wherein said calcining is at from 300°–400° C.

8. The process of claim 6, wherein said intimate dry mix is prepared by wet solution or suspension mixing and then drying.

* * * * *